United States Patent [19]

Burdett

[11] 4,278,809

[45] Jul. 14, 1981

[54] PROCESS FOR PREPARING 2-ISOCYANATOALKYL ESTERS OF ORGANIC CARBOXYLIC ACIDS

[75] Inventor: Kenneth A. Burdett, Midland, Mich.

[73] Assignee: The Dow Chemical Company, Midland, Mich.

[21] Appl. No.: 806,805

[22] Filed: Jun. 15, 1977

[51] Int. Cl.$^3$ ............................................. C07C 67/18
[52] U.S. Cl. .................................... 560/222; 560/266
[58] Field of Search ............... 560/206, 222, 265, 266; 260/307 F, 453 P

[56] References Cited

U.S. PATENT DOCUMENTS 3,535,332  10/1970  Runge et al. ..................... 260/307 F

FOREIGN PATENT DOCUMENTS 1252099  11/1971  United Kingdom .

OTHER PUBLICATIONS

Seelinger, W. et al. "Recent Synthesis and Reactions of Cyclic Imidic Esters." Angew. Chem., Internat. Ed. vol. 5. No. 10 (1966) at p. 882.

*Primary Examiner*—Natalie Trousof
*Assistant Examiner*—L. Hendriksen
*Attorney, Agent, or Firm*—L. Wayne White; Michael L. Glenn

[57] ABSTRACT

2-Isocyanatoalkyl esters of organic carboxylic acids are prepared by reacting (a) an aqueous solution of a 2-oxazoline with (b) an organic solution of phosgene dissolved in a water-immiscible organic solvent in the presence of (c) a hydrochloric acid acceptor. As an example, 2-isocyanatoethyl methacrylate was prepared by concurrently blending an aqueous stream of 2-isopropenyl-2-oxazoline, a methylene chloride stream of phosgene and an aqueous stream of sodium hydroxide at a temperature of from about 0° C. to about 10° C. The reaction rate is very high and the reaction is essentially complete upon blending the reactants.

4 Claims, No Drawings

4,278,809

PROCESS FOR PREPARING 2-ISOCYANATOALKYL ESTERS OF ORGANIC CARBOXYLIC ACIDS

BACKGROUND OF THE INVENTION

1. Field of the Invention

This is a novel process which produces 2-isocyanatoalkyl esters of organic carboxylic acids in high yields. This process is particularly useful in preparing 2-isocyanatoalkyl esters of alkenoic acids.

2. Prior Art

The 2-substituted-2-oxazolines form a known class of compounds. The literature is replete with information regarding methods of preparation and use of such compounds. See, for example, the following review articles: (a) Wiley et al., *Chemical Reviews*, Vol. 44, 447 (1949); (b) Seeliger et al., *Angew. Chem. Internat. Edit.*, Vol. 5, 10 (1966); and (c) Frump, *Chemical Reviews*, Vol. 71, 5 (1971). See also the patents classified by the U.S. Patent and Trademark Office under 260/307F.

The 2-alkenyl-2-oxazolines are particularly useful compounds due to their difunctionality. Of these, the 2-vinyl- and 2-isopropenyl-2-oxazolines are perhaps the best known. Prior art methods of preparing 2-alkenyl-2-oxazolines normally utilize relatively expensive reagents in multistep processes and the product yields were normally low. See, for example, the processes described in the above review articles and refer to the following U.S. Pat. Nos.: 2,831,858; 2,968,657; 3,248,397; 3,466,308; 3,505,297; 3,523,123; 3,535,332; 3,661,922; 3,678,065; 3,839,350; Fr. Pat. No. 1,557,954 and Ger. Offen. No. 2,302,168.

Another process for preparing 2-alkenyl-2-oxazolines was described by Lalk et al. in a commonly-owned U.S. patent application Ser. No. 699,091 filed June 23, 1976 and entitled "Method for Preparing 2-Alkenyl-2-Oxazolines." The disclosure of Ser. No. 699,091 is incorporated herein by reference. The process described in Ser. No. 699,091 comprises the steps of:

(1) reacting by contacting an anhydrous or substantially anhydrous 2-alkyl-2-oxazoline with formaldehyde in a molar ratio of at least about 1.5 mole of 2-alkyl-2-oxazoline per mole of formaldehyde, thereby forming the 2-(α-hydroxymethylalkyl)-2-oxazoline, (2) recovering the 2-(α-hydroxymethylalkyl)-2-oxazoline from the reaction product of step (1), and (3) reacting by contacting the 2-(α-hydroxymethylalkyl)-2-oxazoline from step (2) with an alkali or alkaline earth metal hydroxide, thereby forming the 2-alkenyl-2-oxazoline.

The 2-alkenyl-2-oxazoline thus produced is normally recovered by distillation as an aqueous solution. Water is formed as a by-product of the process and normally codistills with the 2-alkenyl-2-oxazoline. This crude aqueous 2-alkenyl-2-oxazoline is surprisingly useful in the instant process; it can be added per se into the reaction process, but, we prefer to dilute it with sufficient water to give about a 20 mole percent solution of oxazoline in water, and we most prefer to dilute to about a 5–10 mole percent concentration.

The use of a crude aqueous 2-alkenyl-2-oxazoline as prepared by the above process or any aqueous solution of a 2-oxazoline in the preparation of 2-isocyanatoalkyl esters of organic carboxylic acids is in direct contrast to the teachings of British Pat. No. 1,252,099. In the British patent, a 2-oxazoline dissolved in a water-immiscible solvent was reacted with phosgene (also dissolved in a water-immiscible solvent) in the presence of an aqueous solution of a hydrochloric acid acceptor.

SUMMARY OF THE INVENTION

A new process for preparing 2-isocyanatoalkyl esters of organic carboxylic acids has been discovered. The novel process comprises reacting by contacting:

(a) an aqueous solution of a 2-oxazoline, and (b) an organic solution of phosgene dissolved in a water-immiscible organic solvent, in the presence of (c) a hydrochloric acid acceptor.

The instant process represents a substantial advantage over the closest known art (namely, British Pat. No. 1,252,099) in that the costly and difficult procedure of obtaining anhydrous 2-oxazolines is eliminated and the volume of water-immiscible organic solvents is substantially reduced which results in further economy. Further, there is a substantial advantage in the instant process in terms of occupational safety when dealing with the 2-alkenyl-2-oxazolines. The 2-alkenyl-2-oxazolines (particularly the lower molecular weight compounds, such as 2-vinyl- and 2-isopropenyl-2-oxazoline) are treated as a toxic class of compounds. In the instant process, there is less "handling" of the 2-alkenyl-2-oxazolines because the steps of isolating, drying and redissolving the 2-alkenyl-2-oxazoline in an organic solvent have been eliminated. Thus, the chance of contact exposure has been statistically reduced. Further, an aqueous solution of the 2-alkenyl-2-oxazolines will normally have a lower vapor pressure than a solution of the 2-alkenyl-2-oxazoline in a water-immiscible organic solvent (such as methylene chloride, the solvent of choice). Therefore, the potential exposure by inhalation has been reduced. These improvements which result in economic and safety advantages over the prior art are commercially significant.

The instant process is also a significant advance of the more conventional preparation of isocyanates by the direct phosgenation of anhydrous amines in the presence of hydrochloric acid. Such processes tended to require rigorous process conditions, long reaction times, a large excess of phosgene and anhydrous hydrochloric acid. In contrast, the instant process can be conducted under extremely mild conditions to give the desired product in high yields and is substantially instantaneous. Further, the instant process does not require any substantial excess of phosgene or a phosgene recovery system and it does not require the use of anhydrous hydrochloric acid. These advantages are likewise of significant commercial importance.

DETAILED DESCRIPTION OF THE INVENTION

The 2-oxazolines form a known class of compounds having many members, any member of which can be used herein so long as the compound is water-miscible or water-soluble to the extent of at least about 5 weight percent in water. Such oxazoline reactants can bear inert ring substituents (e.g., alkyl groups, etc.) in the 4- and/or 5-ring positions and can be mono- or bisoxazolines. Preferred reactants correspond to the formula:

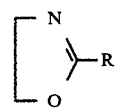   I wherein R is hydrogen or lower alkyl or lower alkenyl groups of from 1 to about 4 carbon atoms. The most preferred reactants are 2-vinyl-2-oxazoline and 2-isopropenyl-2-oxazoline. Other suitable reactants include, for example, those of formula I wherein R is hydrogen, methyl, ethyl, propyl, and the like, and 4-methyl-2-oxazoline, 4-ethyl-2-methyl-2-oxazoline, 4,4-dimethyl-2-methyl-2-oxazoline, 4,5-dimethyl-2-ethyl-2-oxazoline, 4-carbethoxymethyl-2-methyl-2-oxazoline, 1,4-tetramethylene bis(2-oxazoline), and the like. These oxazolines are used in the instant process as aqueous solutions thereof.

Phosgene ($COCl_2$) is a gas and is used in the instant process as a solution thereof in an inert water-immiscible organic solvent. Examples of suitable solvents include hydrocarbons (e.g., hexane, cyclohexane, petroleum ether, benzene, toluene, xylene, diisopropylbenzene, and other such normally liquid hydrocarbons), chlorinated hydrocarbons (such as methylene chloride, chloroform, chlorobenzene, o-dichlorobenzene, etc.), and other like compounds. Mixtures of such inert solvents can likewise be used. Methylene chloride is the solvent of choice.

Hydrochloric acid is produced as a by-product of the instant process and could lead to undesired by-products. The instant process is therefore conducted in the presence of a hydrochloric acid acceptor which neutralizes the hydrochloric acid essentially as it is formed. Suitable hydrochloric acid acceptors include both inorganic and organic bases but the water-soluble inorganic bases are preferred due to cost, ease of handling, etc. Examples of suitable such hydrochloric acid acceptors include sodium and potassium hydroxides, sodium and potassium carbonates, sodium and potassium phosphates, triethylamine, pyridine, and the like. Sodium hydroxide is the most preferred acid acceptor because of its commercial availability and relative cost.

The stoichiometry of the instant process requires 1 mole of phosgene, two equivalents of base and 1 mole of water per mole of 2-oxazoline in the process. We prefer to use a slight excess of phosgene and a slight excess of base (relative to the amount of phosgene) in the process and we prefer to use water in the instant process in amounts substantially exceeding stoichiometric amounts. Water functions in the process as a reactant, as a solvent for the oxazoline reactant, as a solvent for the salt formed from the reaction of hydrochloric acid and the hydrochloric acid acceptor and as a liquid reaction medium. Water is therefore added in amounts sufficient to satisfy stoichiometry and also to provide a liquid aqueous phase in the reaction mixture. We normally prefer to use at least about 15 moles of water per mole of oxazoline reactant and most prefer to use at least about 25 moles of water per mole of oxazoline reactant.

The instant process is normally conducted at a reaction temperature of from about −30° C. to about 25° C.; preferably, from about −10° C. to about 15° C.; and more preferably, from about 0° C. to about 10° C.

The instant process is preferably conducted by simultaneously introducing a precooled aqueous solution of the 2-oxazoline, a precooled organic solution of phosgene and a precooled aqueous solution of the hydrochloric acid acceptor into a reaction vessel with vigorous stirring and cooling. The reaction is essentially instantaneous and is normally complete upon thorough mixing of the reactants. The instant process can be conducted batchwise or in a continuous fashion.

The 2-isocyanatoalkyl ester of the organic carboxylic acid is recovered from the organic phase of the reaction mixture by conventional techniques (e.g., distillation). Product yields are maximized by recovering the product from the organic phase as soon as practical. This minimizes losses due to hydrolysis.

EXPERIMENTAL

The following examples will further illustrate the invention.

EXAMPLE 1

Preparation of 2-Isocyanatoethyl Formate

A 3-liter jacketed reactor equipped with an overhead stirrer and a pH electrode was charged with 288 ml of methylene chloride, 63 ml of water and cooled to approximately 0° C. An aqueous solution of 2-H-2-oxazoline (64.6 g) in 114 ml of water and a solution of phosgene (131 g) in 280 ml of methylene chloride and 250 ml of a 35 weight percent aqueous sodium hydroxide solution were charged simultaneously to the reaction vessel with stirring and cooling. The rates of addition were such that the total addition time of each was approximately 55 minutes. During the reaction, the pH decreased from 13.8 to 7.5. Stirring was continued for approximately 2 minutes and the layers separated. The organic layer was isolated, dried over anhydrous sodium sulfate, and the desired reaction product distilled therefrom at 69°/7.7 mm Hg. The product was thus obtained as a clear, colorless liquid weighing 30.6 g (30 percent of theory). The product structure was confirmed by infrared and nuclear magnetic resonance spectroscopy.

EXAMPLE 2

Preparation of 2-Isocyanatoethyl Acetate

In like manner, a 3-liter jacketed reaction vessel was charged with 288 ml of methylene chloride and cooled to 0° C. A solution of 2-methyl-2-oxazoline (77.5 g) in 137.7 ml of water, a solution of phosgene (131 g) in 280 ml of methylene chloride, and 250 ml of a 35 weight percent solution of aqueous sodium hydroxide were added simultaneously to the reaction vessel with cooling and stirring; the total additive time was approximately 55 minutes. Stirring was continued for 2 minutes after the addition was complete and the organic and aqueous layers then allowed to separate. The organic layer was isolated and dried over anhydrous sodium sulfate, and concentrated under reduced pressure. The desired product was then obtained from the concentrated organic layer by distillation at 55°/5 mm Hg to give 74.8 g (65 percent of theory) of the desired product as a clear, colorless liquid. The product structure was likewise confirmed by infrared and nuclear magnetic resonance spectroscopy.

EXAMPLE 3

Preparation of 2-Isocyanatoethyl Propionate

Using the technique set forth in Example 1 above, the title compound was prepared in 42 percent yield based on theory.

EXAMPLE 4

Preparation of 2-Isocyanatoethyl Methacrylate

A 3-liter jacketed reactor vessel was charged with 100 ml of methylene chloride and cooled to approximately 0° C. A solution of 2-isopropenyl-2-oxazoline (100 g) in 177 ml of water, a solution of phosgene (131.5 g) in 400 ml of methylene chloride, and a solution of 35 weight percent sodium hydroxide in water were added simultaneously to the reaction vessel with stirring and cooling. The rates of addition were such that the three reagents were added over approximately a 50 minute time span with the temperature being maintained at 10° to 18° C. Stirring was continued for two minutes and the layers allowed to separate. The organic layer was washed twice with 100 ml portions of a saturated aqueous sodium bicarbonate solution, dried over sodium sulfate and concentrated under reduced pressure. The colorless concentrate was inhibited with 0.1 g of phenothiazine and the desired product recovered therefrom as a colorless liquid (133.6 g) boiling at 46°–47° C./0.4 mm Hg. Product yield 95–96 percent of theory.

EXAMPLES 5–8

Preparations of 2-Isocyanatoethyl Methacrylate

A 20 gallon glass-lined jacketed reactor equipped with a recycle line and heat exchanger was charged with 9,979 g of methylene chloride (two gallon) and 11,340 g (3 gallons) of water. The recycle pump was started and the reactor cooled to approximately 0° C. A solution of 2-isopropenyl-2-oxazoline (2,268 g) in 7,598 g of water, a solution of phosgene (2,977 g) in 11,340 g of methylene chloride, and a solution of 35 percent sodium hydroxide (approximately 9,525 g) were added simultaneously to the reactor with stirring and cooling during a time period of approximately 65 minutes. The reaction temperature rose to approximately 16° C. during the course of the addition. Stirring at 116 rpm was continued for an additional 3 minutes. The aqueous and organic layers were allowed to separate and the organic layer recovered. The organic layer was then dried by passing it through 3 angstrom molecular sieves and inhibited with 25 g of phenothiazine and concentrated under reduced pressure. A final vacuum distillation at 46°–47° C./0.4 mm Hg gave 2,681 g of 2-isocyanatoethyl methacrylate for an 84.7 percent yield. In three other duplicate runs, the yields range from 78 percent to the above 84.7 percent yield. This is an average of 82 percent over the 4 runs.

Other 2-isocyanatoalkyl esters of carboxylic acids can be similarly prepared using other oxazoline reactants as set forth aove.

What is claimed is:

1. A process for preparing a 2-isocyanatoalkyl ester of an organic carboxylic acid comprising reacting by contacting
    (a) an aqueous solution of a 2-oxazoline, and
    (b) a solution of phosgene in a water-immiscible organic solvent, in the presence of
    (c) a hydrochloric acid acceptor, wherein (a), (b), and (c) are added essentially simultaneously to a reaction vessel with efficient blending in essentially stoichometric amounts.

2. The process defined by claim 1 wherein (a) is an aqueous solution of 2-vinyl- or 2-isopropenyl-2-oxazoline, (b) is a methylene chloride solution of phosgene, (c) is an aqueous solution of sodium hydroxide, and wherein the reaction temperature is from about −10° C. to 15° C.

3. A process for preparing a 2-isocyanatoalkyl ester of an organic carboxylic acid comprising reacting by contacting
    (a) an aqueous solution of a 2-oxazoline, and
    (b) a solution of phosgene in a water-immiscible organic solvent, in the presence of
    (c) a hydrochloric acid acceptor, wherein said process is conducted by simultaneously introducing a precooled aqueous solution of said 2-oxazoline, a precooled organic solution of phosgene, and a precooled aqueous solution of the hydrochloric acid acceptor into a reaction vessel with vigorous stirring and cooling; water being present in said reaction mixture in an amount sufficient to satisfy stoichiometry of the reaction and to provide a liquid aqueous phase in the reaction mixture and said reaction temperature being maintained between about −30° C. and about 25° C.

4. The process defined by claim 3 wherein (a) is an aqueous solution of 2-isopropenyl-2-oxazoline, (b) is a methylene chloride solution of phosgene, (c) is an aqueous solution of sodium hydroxide and said reaction temperature is maintained from about −10° C. to about 15° C.

* * * * *